May 5, 1942. F. BROCKNER Plant Pat. 514
SAINTPAULIA PLANT
Filed Jan. 2, 1942
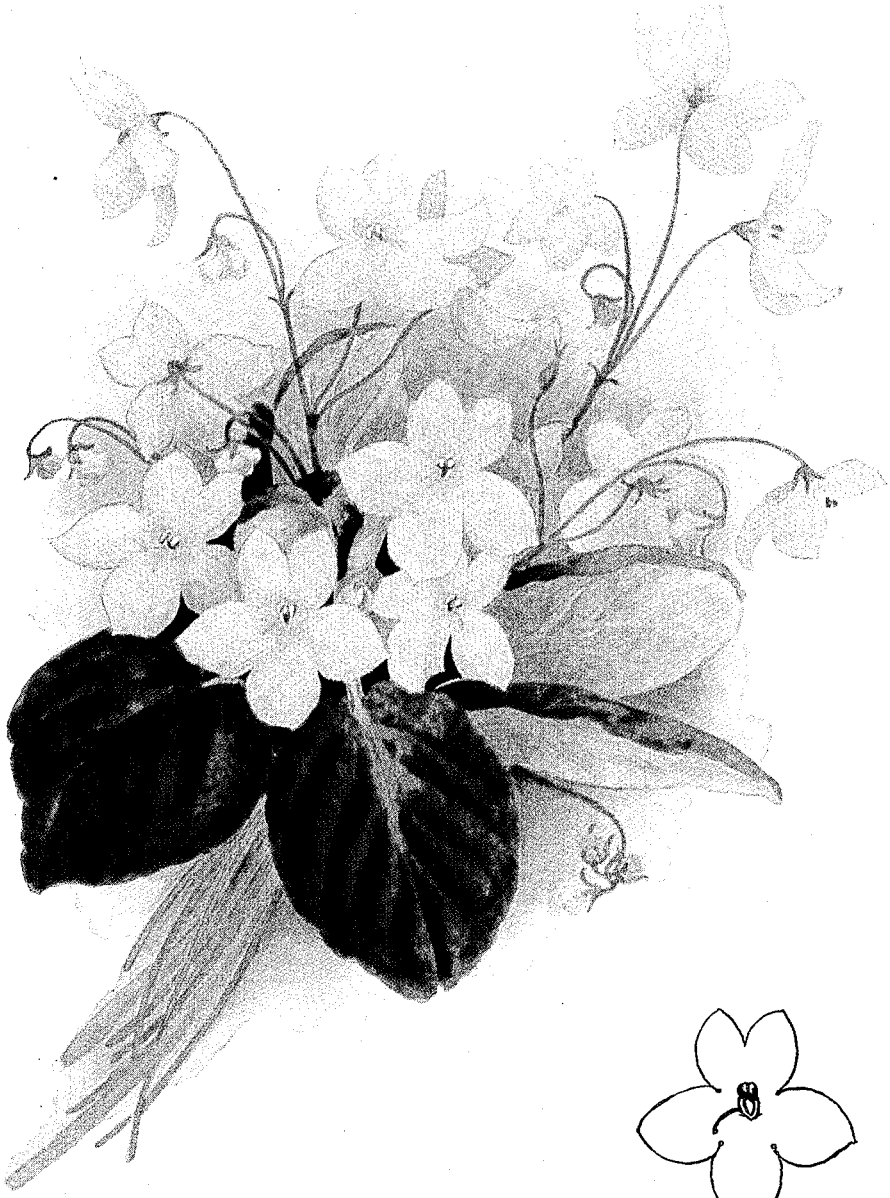
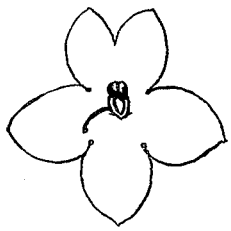
Inventor
Frank Brockner
Witness
Addison E Avery
By: Rummler Rummler & Davis
his Attys.

Patented May 5, 1942

Plant Pat. 514

UNITED STATES PATENT OFFICE

514

SAINTPAULIA PLANT

Frank Brockner, Milwaukee, Wis., assignor to Holton & Hunkel Co., Milwaukee, Wis., a corporation of Wisconsin Application January 2, 1942, Serial No. 425,415

1 Claim. (Cl. 47—60)

The present discovery relates to a new and distinct variety of *Saintpaulia ionantha* plant, originating as a sport of the well-known variety "Blue Boy." It has been asexually reproduced by cuttings since August, 1940, and its characteristics appear to be permanently fixed.

The new Saintpaulia plant is distinguishable from the parent plant mainly in the color of its blossoms and leaves. The flowers are of a distinctively warm, crystalline pink color and the smooth-edged leaves a soft greenish color with an overtone of silver.

The purpose of this breeding effort was to produce a healthy strong-growing Saintpaulia plant with pure pink blossoms of good size and substance.

This new variety in plant structure is similar to the parent plant *Saintpaulia (ionantha)* "Blue Boy" except for the color of the corolla and pistil. The flowers, borne in a loose cyme, have the usual five lobes; wide-campanulate corolla; and small calyx. The pilose leaves are long-petioled, and ovate in shape.

The accompanying illustration shows, in full color, typical blossoms and leaves, and at the side of the painting a detail of the blossom.

The profusion of blossoms of a clear pink tone with their conspicuous, yellow stamens protruding like tusks from the center of each flower; compact foliage, with each leaf outstanding because of its soft green upper surface and silvery nether surface lined with prominent pinkish veins, together with the symmetry of form of the plant as a whole; its superior keeping qualities and resistance to disease, combine to provide a very desirable, rare, and exquisite commercial product.

The following is a detailed description of the new variety:

*Flower*

Blooming habit: Recurrent—5 to 6 weeks.
Size: 37 mm.
Form: Corolla is wide—campanulate.
Borne: In a loose cyme—1 to 6 flowered.
Shape: Corolla lobes, elliptic, but not equal.
Texture: Crystalline.
Stems: Green shaded into pink.
Discoloration: None.
Affected by wet or hot weather: No, except extremes.
Persistence (hang on and dry): Bloom lasts about 2 to 3 weeks and then dries and drops.
Disease resistant: Yes (no disease noted).

*Bud*

Color: New Silver+.
Sepals: 5.
Calyx: Deeply 5-lobed (lance-shaped).

*Genital organs*

Stamens-anthers: 2 stamens 3 mm. wide, 2 mm. long borne on a filament 4 to 5 mm. long.
*Arrangement*: Epipetalous.
*Pollen*: Color—yellow.
*Styles*: Number, 1; length, 9 mm.
*Stigma*: Color, pale amaranth pink.

*Foliage*

Quantity: Abundant.
Color: Upper side of leaves—art green. Underside of leaves—silver toned.
Size: 5.2 mm. long; 4.6 mm. wide.
Hairy: Fine white hairs.
Shape: Blunt pointed, smooth-edged, ovate.

The color designations according to "A Dictionary of Color by Maerz and Paul" are as follows:

| | Color | Plate | Letter | Number |
|---|---|---|---|---|
| Main body of flower | | 41 | F | 2 |
| Darker section at center. | | 41 | I | 3 |
| Stamens | | 9 | L | 5 |
| Larger buds | New Silver+ | 11 | B | 1 |
| Peduncle at top near blossoms. | | 6 | H | 9 |
| Shading into paler color at base. | | 14 | I | 5 |
| Main body of leaf | Art green | 22 | L | 7 |
| Under side of leaf | | 17 | B | 2 |
| Large veins on under side of leaf. | | 3 | B | 2 |
| Petioles | | 13 | D | 5 |

This new variety of Saintpaulia is easily distinguished from other varieties by its unusual coloring and fullness of bloom.

Having thus disclosed the invention, I claim:

A new and ornamental variety of Saintpaulia plant with features in combination substantially as shown and described, characterized particularly by the unusual warm pink color of its blossoms, brilliant yellow color of its stamens, fullness of bloom, symmetrical proportions of the plant as a whole, and sturdy stems.

FRANK BROCKNER.